(12) United States Patent
You

(10) Patent No.: US 6,398,806 B1
(45) Date of Patent: Jun. 4, 2002

(54) MONOLAYER MODIFICATION TO GOLD COATED STENTS TO REDUCE ADSORPTION OF PROTEIN

(75) Inventor: Chuanting You, Brooklyn Park, MN (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/681,080

(22) Filed: Dec. 26, 2000

(51) Int. Cl.⁷ .................................................. A61F 2/06
(52) U.S. Cl. ..................................... 623/1.15; 623/1.43
(58) Field of Search ............................. 623/1.11–1.15, 623/1.46, 23.7; 427/2.25

(56) References Cited

U.S. PATENT DOCUMENTS

| | | | | |
|---|---|---|---|---|
| 5,059,166 A | * | 10/1991 | Fischell et al. ............. | 623/1.15 |
| 5,770,645 A | * | 6/1998 | Stamler et al. ............. | 524/419 |
| 5,824,045 A | | 10/1998 | Alt ................................ | 623/1 |
| 5,957,930 A | | 9/1999 | Vrba ........................... | 606/108 |
| 6,087,479 A | | 7/2000 | Stamler et al. ............. | 530/363 |
| 6,099,561 A | | 8/2000 | Alt .............................. | 623/1.44 |
| 6,120,522 A | | 9/2000 | Vrba et al. .................. | 606/190 |
| 6,123,712 A | | 9/2000 | Di Caprio et al. .......... | 606/108 |
| 6,159,142 A | | 12/2000 | Alt ............................... | 600/3 |
| 6,171,232 B1 | * | 1/2001 | Papandreou et al. ....... | 623/1.42 |
| 6,174,326 B1 | | 1/2001 | Kitaoka et al. .............. | 623/1 |
| 6,174,329 B1 | | 1/2001 | Callol et al. ................ | 623/1.34 |
| 6,174,539 B1 | | 1/2001 | Stamler et al. ............. | 424/422 |
| 6,232,434 B1 | * | 5/2001 | Stamler et al. ............. | 528/373 |
| 6,255,277 B1 | | 7/2001 | Stamler et al. ................. | 514/2 |

FOREIGN PATENT DOCUMENTS

EP 916317 5/1999

OTHER PUBLICATIONS

U.S. application No. 09/659,571, Olson et al., filed Sep. 12, 2000.
U.S. application No. 09/697634, DiCaprio, filed Oct. 26, 2000.
Cahikol et al. "Self–assembling Peptide Monolayers: Endothelial Cell Behavior on Functionalized Metal Substrates" Mat. Res. Soc. Symp. Proc. vol. 414 Copyright 1996 Materials Research Society pp. 17–22.*

* cited by examiner

Primary Examiner—Kevin Truong
Assistant Examiner—Tan-Uyen T. Ho
(74) Attorney, Agent, or Firm—Vidas, Arrett & Steinkraus, PA

(57) ABSTRACT

A stent has a body and a surface with at least a portion of the surface comprising metal with a coating thereon. The coating is selected from the group consisting of thiols and disulfides and combinations thereof. The thiols are of the form R—SH and the disulfide of the form R—S—S—R" where R is an alkyl group and R" is an alkyl group. The metal is selected from the group consisting of noble metals, silver and copper.

28 Claims, 3 Drawing Sheets

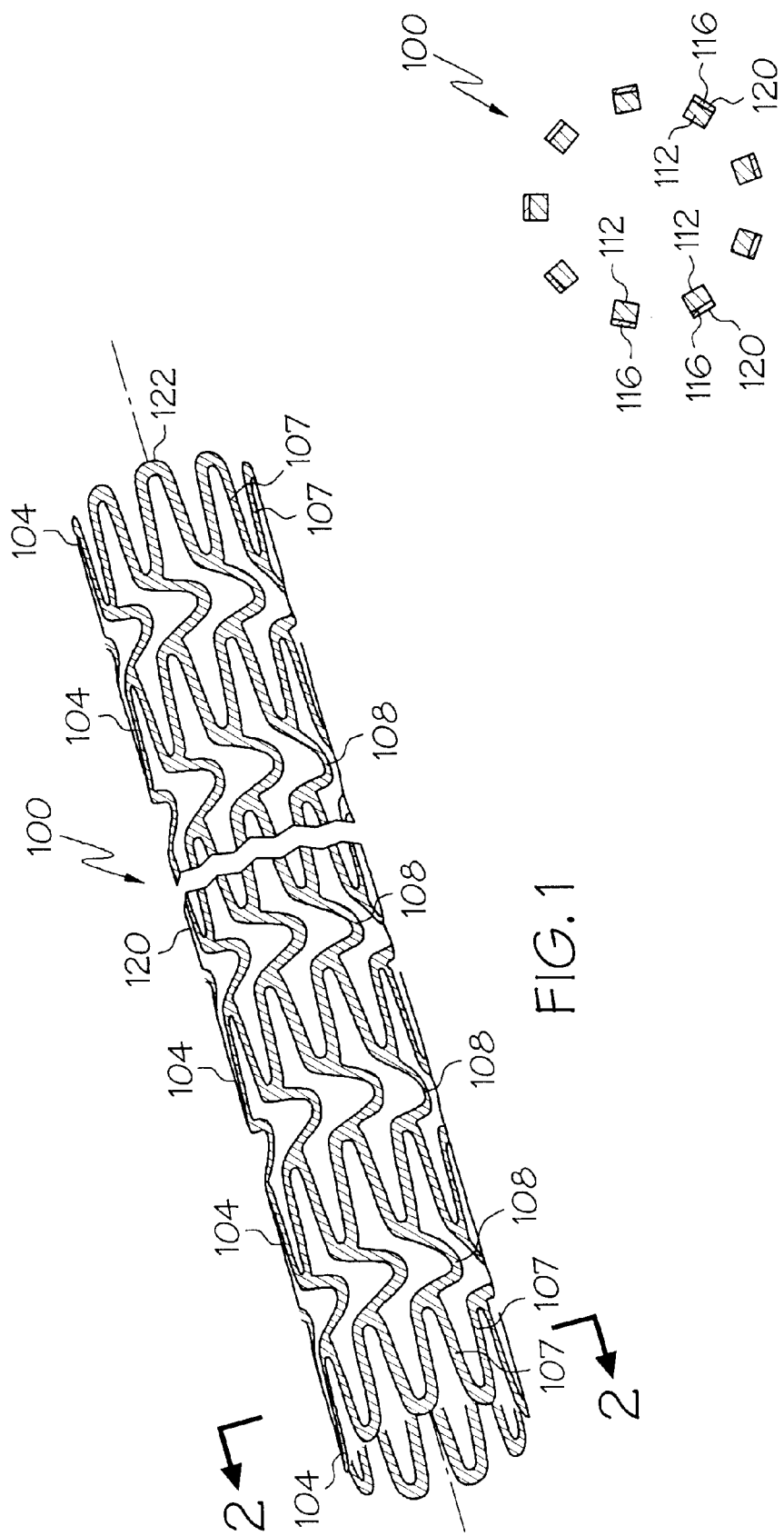

MONOLAYER MODIFICATION TO GOLD COATED STENTS TO REDUCE ADSORPTION OF PROTEIN

BACKGROUND OF INVENTION

The use of gold plated stents is known in the art and is disclosed in a number of patents and patent applications including U.S. Pat. No. 5,824,045, U.S. Pat. No. 6,099,561 and copending and commonly assigned U.S. application Ser. No. 09/697634 filed Oct. 26, 2000. Gold plating increases the radiopacity of the stent, a feature that has proven useful for imaging purposes.

Over time, stents that have been implanted in the body tend, whether gold plated or otherwise, to have proteins adsorbed thereto which increases the likelihood of restenosis. While numerous surface modification treatments to achieve desired surface properties are known for stents, there remains a need for treatment processes for modifying the surface properties of stents having a surface of gold or other noble metals.

For the purposes of this disclosure, the term noble metal shall refer to a metal of the group Ruthenium (Ru), Rhodium (Rd), Palladium (Pd), Osmium (Os), Iridium (Ir), Platinum (Pt), Silver (Ag), and Gold (Au).

All U.S. patents and applications all other published documents mentioned anywhere in this application are incorporated herein by reference in their entirety.

The abstract provided herewith is intended to comply with 37 CFR 1.72 and is not intended to be used in determining the scope of the claimed invention.

Without limiting the scope of the invention in anyway, the invention is briefly summarized in some of its aspects below.

SUMMARY OF INVENTION

The instant invention is directed in at least some of its embodiments to coated stents. Other embodiments of the invention include methods of coating stents.

In one embodiment, the invention is directed to a stent having a body and a surface, at least a portion of the surface comprising a metal with a coating on the metal. The coating is selected from the group consisting of thiols and disulfides and combinations thereof. The thiols are of the form R—SH and the disulfides are of the form R—S—S—R" where R and R" are alkyl groups. Suitably, R has at least 4 carbons. Desirably, R has from 12 carbons to 32 carbons. More desirably R has from 12 to 24 carbons. Suitably, R" has at least 4 carbons. Desirably, R" has from 12 carbons to 32 carbons. More desirably R" has from 12 to 24 carbons. Only a portion of the surface may be metal or, more desirably, the entirety of the surface may comprise the metal. The metal desirably is selected from the group consisting of noble metals, copper and silver and combinations thereof. Where the metal is gold, the gold may be coated on the body of the stent via plating or any other technique. Desirably, the thiol and/or disulfide coating is substantially one monolayer thick.

The invention is also directed to a method of preparing a stent comprising the steps of providing a stent having a surface at least a portion of which is metal and coating the metal surface with a coating moiety selected from the group consisting of thiols and disulfides and combinations thereof. The thiols are of the form R—SH and the disulfides are of the form R—S—S—R" where R is an alkyl group and R" is an alkyl group. Suitably, R has at least 4 carbons. Desirably, R has from 12 carbons to 32 carbons. More desirably R has from 12 to 24 carbons. Suitably, R" has at least 4 carbons. Desirably, R" has from 12 carbons to 32 carbons. More desirably R" has from 12 to 24 carbons. Desirably, the entire surface of the stent is coated in the coating step. Also desirably, the metal is selected from the group consisting of noble metals, copper and silver. More desirably, the metal is gold. In accordance with the inventive method, the coating moiety may be disposed in a solvent such as methanol, ethanol, isopropanol and combinations thereof and the stent placed in the solvent. The coating may be provided via other techniques as well including spraying the coating on the metal surface of the stent. Desirably, the coating is substantially one monolayer thick.

The invention is also directed to a stent at least a portion of which has a substantially monolayer thick coating of one or more members selected from the group consisting of thiols, disulfides, and combinations thereof. Desirably, at least a portion of the stent includes a layer of gold thereon, the monolayer coating disposed on the layer of gold. More desirably, the gold layer and monolayer coating extend over the entirety of the surface of the body portion of the stent.

A detailed description of the invention in its various embodiments is provided below.

BRIEF DESCRIPTION OF DRAWINGS

FIG. 1 shows a perspective view of an inventive stent;

FIG. 2 shows a cross-sectional view of the stent of FIG. 1 taken along line 2—2;

DETAILED DESCRIPTION

Figure 3:
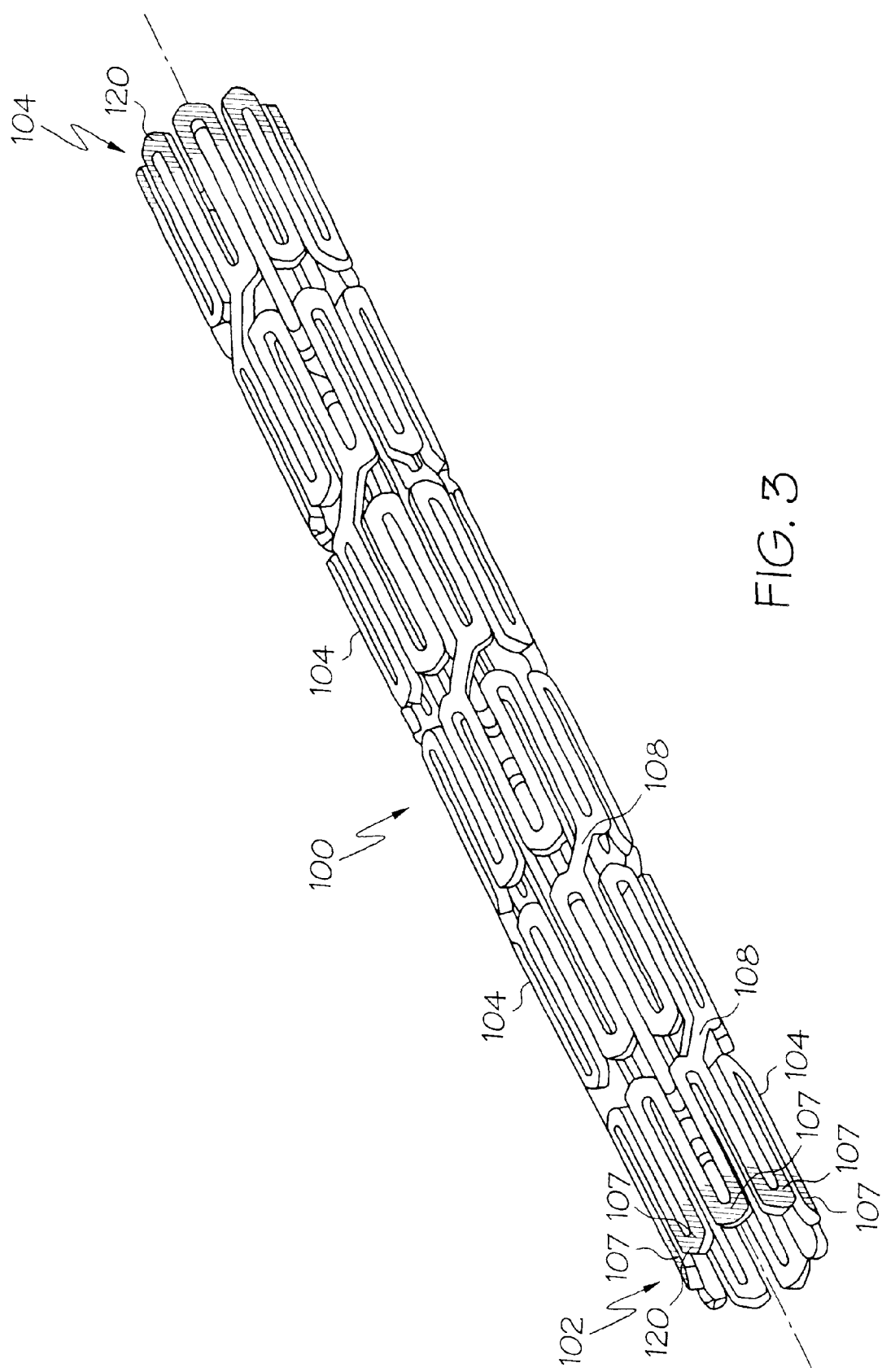
FIG. 3 shows a perspective view of another inventive stent.

For the purposes of this disclosure, unless otherwise indicated, like reference numerals in the figures refer to the same component.

The instant invention is directed in at least some of its embodiments to coated stents. Other embodiments of the invention include methods of coating stents.

The inventive stent may be any suitable stent having a surface at least a portion of which comprises metal with an inventive coating thereon. An example of a stent is shown in FIG. 1 at 100. Stent 100 comprises a plurality of serpentine segments 104, each of which comprises a plurality of interconnected struts 107. Segments 104, which are adjacent one another are connected together via connectors 108. As shown in FIG. 1, connectors 108 have at one bend therein. The connectors may also be provided with a plurality of bends or may substantially linear or rectilinear. The instant invention may be practiced using a stent such as that shown in FIG. 1 or using any other stent geometry. Stent 100 is shown in transverse cross-section in FIG. 2.

The stent includes body 112 and surface 116 as shown in FIG. 2. At least a portion and desirably, the entirety, of surface 116 comprises a metal such as a noble metal, copper, silver or another radiopaque metal. Desirably, the metal is gold. The body of the stent may also comprise the metal or may comprise one or more different metals or polymeric materials. Other suitable metals for the body of the stent include 316L stainless steel, chromium, nickel, titanium, or iridium, or nitinol. Where the body of the stent is of a different metal or other material from the surface metal, the gold or other surface metal may be coated on the body of the stent by plating, painting, swaging, vapor deposition or may be otherwise deposited on the body of the stent. Coating of stents with metals such as gold is discussed in commonly assigned U.S. application Ser. No. 09/659571 as well as in U.S. Pat. No. 5,824,045. As shown in FIGS. 1 and 2, the metal surface of the inventive stents has a coating 120 thereon selected from the group consisting of thiols and disulfides and combinations thereof. The coating is indicated by hatching in FIG. 1. The thiols are of the form R—SH and the disulfides are of the form R—S—S—R" where R is an alkyl group and R" is an alkyl group. Suitably, R has at least 4 carbons. Desirably, R has from 12 carbons to 32 carbons. More desirably R has from 12 to 24 carbons. Suitably, R" has at least 4 carbons. Desirably, R" has from 12 carbons to 32 carbons. More desirably R" has from 12 to 24 carbons. Most desirably, the alkyl group R and/or R" is a 16 carbon alkyl group. Suitably, the alkyl group is a straight chain alkyl group. Desirably, the thiol and/or disulfide coating is substantially one monolayer thick and in the form of a self-arranging monolayer.

The invention is also directed to a stent at least a portion of which has a substantially monolayer thick coating of one or more members selected from the group consisting of thiols, disulfides, and combinations thereof. Desirably, at least a portion of the stent includes a layer of gold thereon, the monolayer coating disposed on the layer of gold. More desirably, the gold layer and monolayer coating extend over the entirety of the surface of the body portion of the stent.

An example of such a stent is shown in FIG. 3. Stent 100 of FIG. 3 includes a plurality of serpentine segments 104. Each serpentine segment comprises a plurality of interconnected struts 107. Adjacent serpentine segments 104 are connected by substantially linear connectors 108 extending therebetween. Proximal end 101 and distal end 102 include a surface layer of metal such as gold. The surface layer is coated with a coating comprising a thiol, disulfide, or both as discussed above. The coating is indicated by hatching in the figure.

Figure 4:
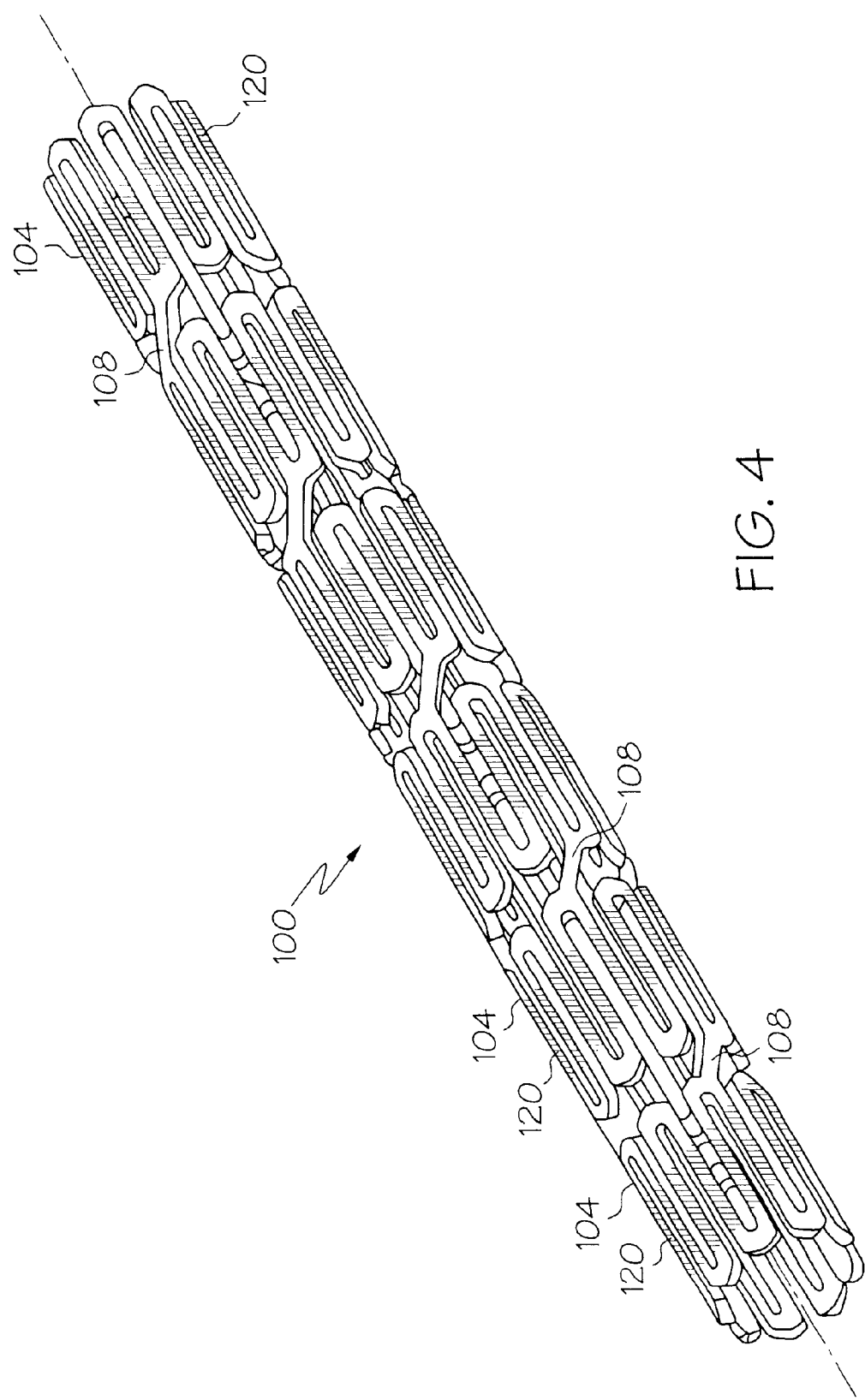
FIG. 4 shows a perspective view of another inventive stent.

Yet another example of such a stent is shown generally at 100 in FIG. 4. Stent 100 includes bands of metals such as noble metals, or silver which are coated with a coating 120 comprising a thiol, disulfide, or both as discussed above.

It is also within the scope of the invention to coat stents having any other pattern of noble metals, copper and/or silver on the surface of the stent. The coating is desirably limited to the patterned metal. Examples of other specific patterns are shown in U.S. application Ser. No. 09/697634.

The invention is also directed to methods of preparing a stent comprising the steps of providing a stent having a surface at least a portion of which comprises metal and coating at least a portion of the metal with a coating moiety selected from the group consisting of thiols and disulfides and combinations thereof. The metal is desirably a radiopaque metal. Suitable metals include noble metals, copper and silver. The body of the stent may be formed of the same metal as that on the surface of the stent or may be made of a different metal or material. As an example, where the surface metal is a layer of gold, the gold may be providing by plating, painting, swaging, vapor deposition or otherwise depositing it.

As discussed above, the thiols are of the form R—SH and the disulfides are of the form R—S—S—R" where R is an alkyl group and R" is an alkyl group. Suitably, R has at least 4 carbons. Desirably, R has from 12 carbons to 32 carbons. More desirably R has from 12 to 24 carbons. Suitably, R" has at least 4 carbons. Desirably, R" has from 12 carbons to 32 carbons. More desirably R" has from 12 to 24 carbons. Most desirably, the alkyl group R and/or R" is a 16 carbon alkyl group. Suitably, the alkyl group is a straight chain alkyl group.

In accordance with the invention, the coating moiety may be applied to the surface metal through any suitable technique. One suitable method involves providing the coating moiety in a solvent. Suitable solvents include methanol, ethanol and isopropanol. Desirably, the concentration of the coating moiety in the solvent is between about 0.1 mM (millimolar) and 10 mM. The stent may be dipped in the solvent or the solvent sprayed on the stent. In the former case, using the concentrations disclosed above, the stent is desirably dipped in the solvent for a period of from about 0.5 hour to about 24 hours. During this time, the coating moiety desirably forms a self-arranging monolayer on the metal surface. Where the solvent is sprayed on the metal surface of the stent, the concentration of the coating moiety is desirably significantly greater than the above-mentioned values to facilitate the formation of a self-arranging monolayer on the stent.

After the coating moiety is applied to the stent, the stent may be removed from the solvent or spraying of the stent ceased and the stent allowed to dry.

Where only portions of the stent have a noble metal, silver or copper thereon, the noble metal, silver or copper may selectively be coated by masking those portions of the stent which do not have the metal thereon so that only the relevant portions of the stent are exposed for coating.

The invention is also directed to stents made using any of the inventive techniques disclosed herein.

The inventive stents may be used for coronary arteries, peripheral arteries, arteries of the neck and intracranial arteries. More generally, the inventive stents may be used for any vessel of the human body including but not limited to arteries, veins, biliary ducts, urethras, fallopian tubes, bronchial tubes, the trachea and the esophagus.

Suitable stent delivery devices including those disclosed in U.S. Pat. No. 6,123,712, U.S. Pat. No. 6,120,522 and U.S. Pat. No. 5,957,930 may be used to deliver the inventive stents to the desired bodily location. The choice of delivery device will depend on whether a self-expanding or balloon expandable stent is used.

In addition to the specific embodiments claimed below, the invention is also directed to other embodiments having any other possible combination of the dependent features claimed below in combination with the independent claims from which they depend.

The above disclosure is intended to be illustrative and not exhaustive. The description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A stent having a body and a surface, at least a portion of the surface comprising a metal with a coating thereon, the metal selected from the group consisting of noble metals, copper and silver and combinations thereof, the coating selected from the group consisting of thiols and disulfides and combinations thereof, the thiols of the form R—SH and the disulfide of the form R—S—S—R" where R is an alkyl group and R" is an alkyl group.

2. The stent of claim 1 wherein R has from 12 to 32 carbons.

3. The stent of claim 2 wherein the entire surface is metal and the coating is on the entirety of the surface.

4. The stent of claim 3 wherein the metal is selected from the group consisting of noble metals, copper and silver.

5. The stent of claim 4 wherein the metal is gold.

6. The stent of claim 3 wherein the coating is substantially one monolayer thick.

7. The stent of claim 5 wherein the coating is substantially one monolayer thick.

8. The stent of claim 3 wherein the coating comprises one or more thiols.

9. The stent of claim 8 wherein the one or more thiols includes a thiol where R=16.

10. The stent of claim 8 wherein R is a straight chain alkyl group.

11. The stent of claim 3 wherein the stent has a body portion and the metal surface is coated on the body portion.

12. The stent of claim 11 wherein the metal is gold and the gold surface is plated on the body portion.

13. A method of preparing a stent comprising the steps of: providing a stent having a surface at least a portion of which comprises metal; and coating the metal with a coating moiety selected from the group consisting of thiols and disulfides and combinations thereof, the thiols of the form R—SH and the disulfides of the form R—S—S—R" where R is an alkyl group and R" is an alkyl group.

14. The method of claim 13 wherein R has from 12 to 32 carbons and R" has from 12 to 32 carbons.

15. The method of claim 14 wherein the entire surface of the stent is coated in the coating step.

16. The method of claim 15 wherein the metal is selected from the group consisting of noble metals, copper and silver.

17. The method of claim 16 wherein the metal is gold.

18. The method of claim 17 wherein the coating moiety is disposed in a solvent.

19. The method of claim 18 wherein the solvent is selected from the group consisting of methanol, ethanol, isopropanol and combinations thereof.

20. The method of claim 18 wherein the solvent is methanol.

21. The method of claim 20 wherein the coating moiety comprises a thiol.

22. The method of claim 21 wherein R=16.

23. The method of claim 18 wherein the coating step comprises placing the stent in the solvent.

24. A stent prepared in accordance with the method of claim 14.

25. The stent of claim 24 wherein the coating is substantially one monolayer thick.

26. A stent prepared in accordance with the method of claim 21.

27. A stent prepared in accordance with the method of claim 23.

28. The stent of claim 26 wherein the coating is substantially one monolayer thick.

* * * * *